US00PP26776P3

(12) United States Plant Patent
Bourne

(10) Patent No.: US PP26,776 P3
(45) Date of Patent: May 31, 2016

(54) ***DIANTHUS* PLANT NAMED 'WP13 GIL05'**

(50) Latin Name: *Dianthus×hybrida*
Varietal Denomination: WP13 GIL05

(71) Applicant: Carolyn Grace Bourne, Dawlish (GB)

(72) Inventor: Carolyn Grace Bourne, Dawlish (GB)

( * ) Notice: Subject to any disclaimer, the term of this patent is extended or adjusted under 35 U.S.C. 154(b) by 114 days.

(21) Appl. No.: 14/120,208

(22) Filed: May 6, 2014

(65) Prior Publication Data

US 2014/0338083 P1 Nov. 13, 2014

(30) Foreign Application Priority Data

May 10, 2013 (QZ) ..... PBR 20131279

(51) Int. Cl.
*A01H 5/02* (2006.01)

(52) U.S. Cl.
USPC ..... Plt./273
CPC ..... *A01H 5/0233* (2013.01)

(58) Field of Classification Search
USPC ..... Plt./273, 272, 274
See application file for complete search history.

*Primary Examiner* — June Hwu

(74) *Attorney, Agent, or Firm* — James M. Weatherly; Bethany R. Roahrig; Cochran Freund & Young, LLC

(57) ABSTRACT

A new cultivar of *Dianthus* plant named 'WP13 GIL05' that is characterized by a compact mounding habit, semi-double white flowers with a deep maroon eye, ruffled petals with distinct fimbriated apices, blooming from May through September, with a moderate to strong spicy or clove-like fragrance, glaucous blue green foliage, suitable for use as a flowering plant in pots and containers as well as for use as a cut flower and in bouquets, is disclosed.

2 Drawing Sheets

Genus and species: *Dianthus×hybrida*.
Variety denomination: 'WP13 GIL05'.

CROSS REFERENCE TO RELATED APPLICATIONS

This application claims the benefit of priority under 35 U.S.C. 119 of the earlier application for European Community Plant Variety Rights, which was filed for the instant plant variety on May 10, 2013, Application Number 2013/1279.

BACKGROUND OF THE NEW PLANT

The present invention relates to a new and distinct cultivar of hardy garden pink, that is grown for use as a flowering plant for pots and containers and for planting in the garden and landscape. The new cultivar is known botanically as *Dianthus×hybrida* and will be referred to hereinafter by the cultivar name 'WP13 GIL05'.

'WP13 GIL05' is a complex hybrid plant that is the product of a long term breeding program conducted in a cultivated area of Houndspool, Dawlish, Devon, United Kingdom. 'WP13 GIL05' was selected in 2005 for its semi-double white flowers with deep maroon eye, fringed petal edges, moderate to strong spicy clove-like fragrance and gray-blue foliage.

'WP13 GIL05' arose and was selected as a seedling which resulted from the open pollination of two prior selections of *Dianthus*. The male parent is known as *Dianthus* code name 'Renata' (unpatented and unreleased) and the female plant was unnamed and unreleased, and not retained. The male parent and female parent had both been grown within the inventor's stock of breeding lines.

Asexual reproduction of 'WP13 GIL05' was first accomplished in 2005 in a cultivated area of Houndspool, United Kingdom. The method of asexual propagation used was shoot cuttings. 'WP13 GIL05' was determined to be stable and reproduces true to type in successive generations of asexual propagation via vegetative cuttings.

SUMMARY

The following traits have been repeatedly observed and represent the characteristics of the new *Dianthus* cultivar 'WP13 GIL05'. 'WP13 GIL05' has not been tested under all possible conditions and phenotypic differences may be observed with variations in environmental, climatic and cultural conditions, however, without any variance in genotype.

1. 'WP13 GIL05' exhibits a compact mounding habit.
2. 'WP13 GIL05' bears semi-double white flowers with a deep maroon eye.
3. The petals of 'WP13 GIL05' are ruffled with distinct fimbriated apices.
4. 'WP13 GIL05' blooms from May through September.
5. The flowers of 'WP13 GIL05' exhibit moderate to strong spicy or clove-like fragrance.
6. 'WP13 GIL05' exhibits glaucous blue green foliage.
7. At maturity, the height of the foliage mound of 'WP13 GIL05' is 24 cm, and the width is 19 cm.
8. 'WP13 GIL05' is perennial and is hardy at least to −15° C.
9. 'WP13 GIL05' is suitable for use as a flowering plant in pots and containers, and for use as a cut flower and in bouquets.

COMPARISON WITH PARENTAL LINE AND KNOWN VARIETY

'WP13 GIL05' is distinguishable from the male parent as follows. Whereas the flower shape and color of 'Renata' is similar to 'WP13 GIL05', the vegetative habit of the two varieties is very different. 'Renata' is much less vigorous than 'WP13 GIL05' and exhibits shorter flower stems and a stiffer more erect habit. In addition, the foliage of 'Renata' exhibits shorter and wider leaves than that of 'WP13 GIL05'.

The identity of the female parent is unknown and therefore a comparison is not possible.

The variety of *Dianthus* considered to most closely resemble 'WP13 GIL05' is the semi-double white with maroon eye flowered *Dianthus* 'Brilliant Star' (U.S. Plant Pat. No. 13,025). In comparison with 'WP13 GIL05', the plant of 'Brilliant Star' exhibits less plant vigor and a more compact habit with flowers borne on shorter stems than 'WP13 GIL05'. In addition, the flowers of 'WP13 GIL05' exhibit a distinctly fimbriated petal edge in comparison to 'Brilliant Star' which has a less fringed edge.

BRIEF DESCRIPTION OF THE PHOTOGRAPHS

The accompanying color photographs illustrate the overall appearance of the new *Dianthus* variety 'WP13 GIL05' showing colors as true as it is reasonably possible to obtain in colored reproductions of this type. Colors in the photographs may differ from the color values cited in the detailed botanical description, which accurately describe the actual colors of the new variety 'WP13 GIL05'.

Figure 1:
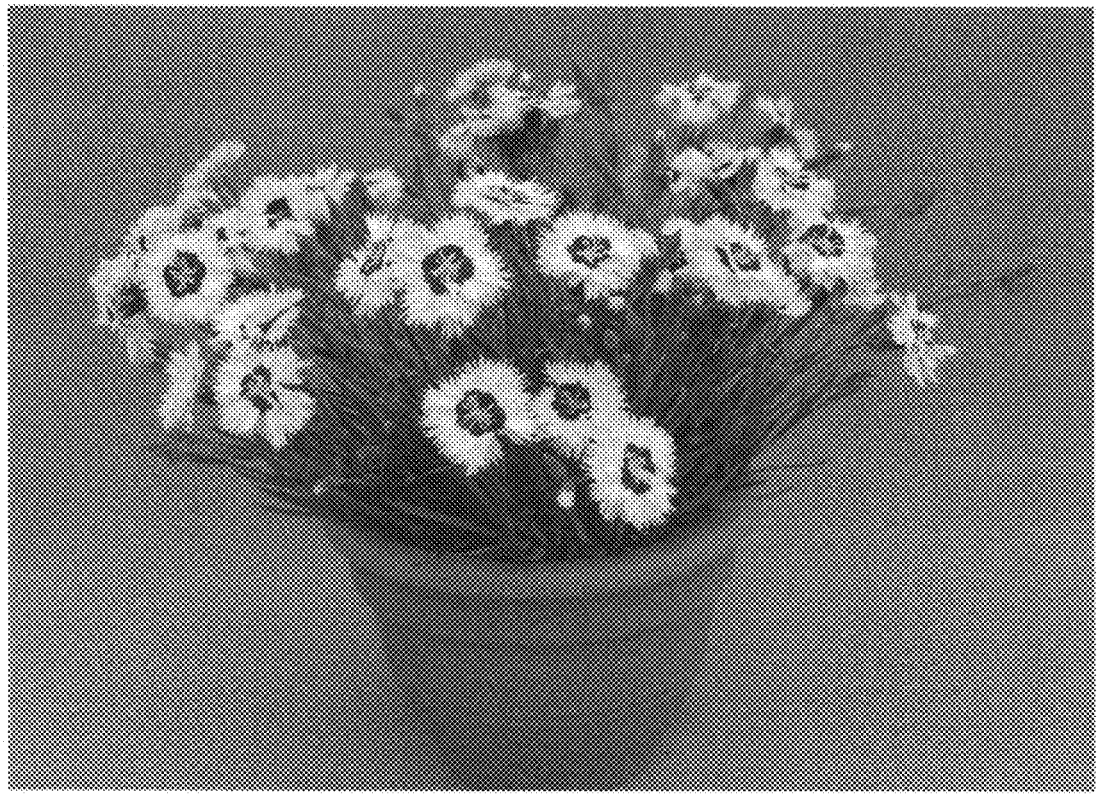
FIG. 1 depicts an entire flowering plant of 'WP13 GIL05'.
Figure 2:
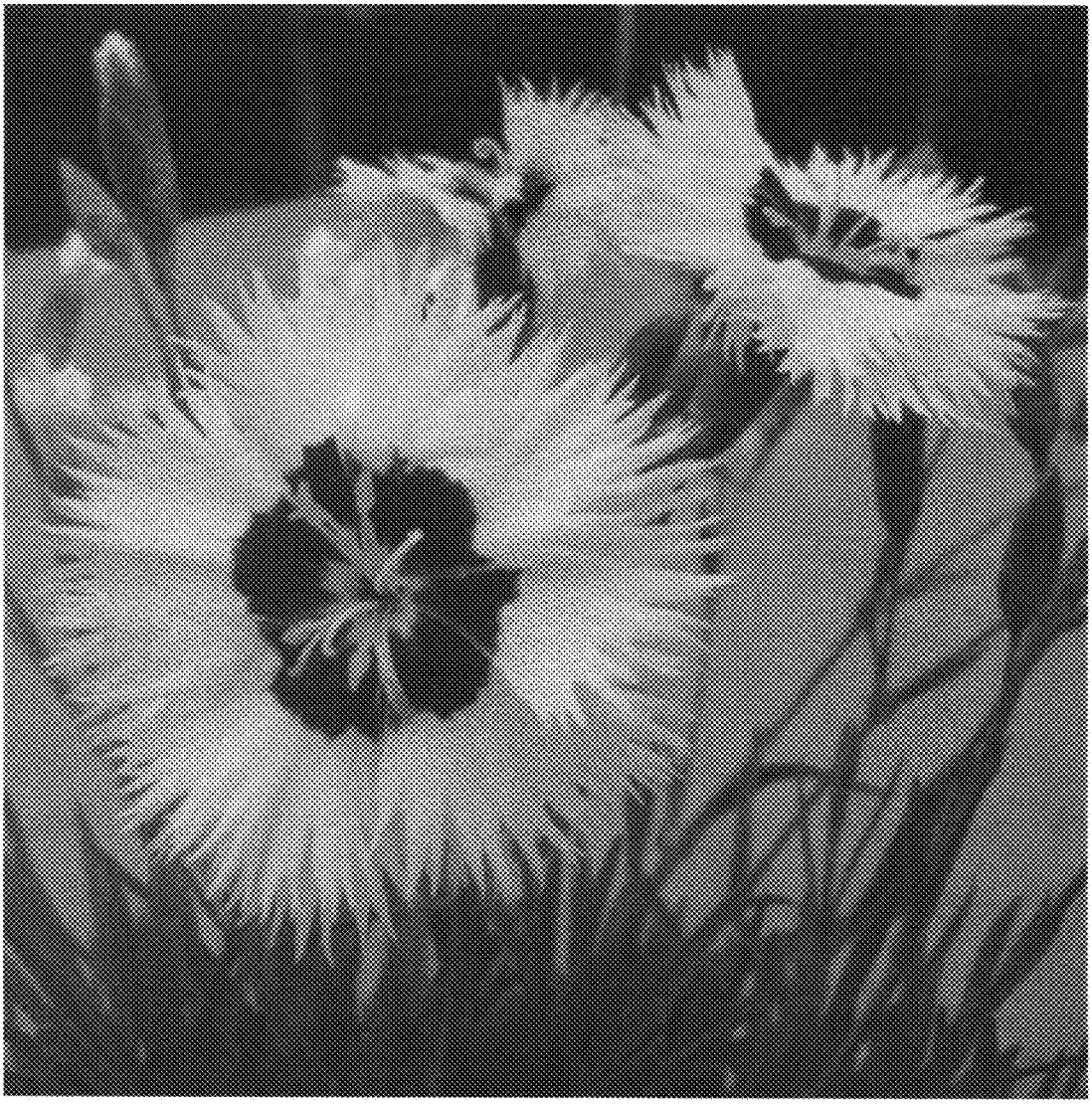
FIG. 2 depicts a close-up view of the flowers and buds of 'WP13 GIL05'.

All photographs were made from one year old plants which have been grown in 1.5-liter containers in a cold glasshouse in Devon, United Kingdom. No chemicals were used to treat the plants.

All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'WP13 GIL05'. Data was collected from plants grown in 1.5 liter containers under an unheated glasshouse in Houndspool, United Kingdom. The color determinations are in accordance with the 2007 edition of The Royal Horticultural Society Colour Chart of The Royal Horticultural Society, London, England, except where general color terms of ordinary dictionary significance are used. No chemicals were used to treat the plants. Growing conditions are typical to other *Dianthus*.

Botanical classification: *Dianthus*.

*Variety*.—'WP13 GIL05'.

*Species*.—×*hybrida*.

*Common name*.—Hybrid *dianthus*.

*Commercial classification*.—Hardy perennial herb.

*Use*.—Ornamental plant for pots and containers.

Parentage: 'WP13 GIL05' is a hybrid plant that resulted from the open pollination of a group of unidentified *Dianthus* seedling varieties.

*Female parent plant*.—*Dianthus* plant (unknown).

*Male parent plant*.—*Dianthus* 'Renata' (unpatented).

Plant description:

*Bloom period*.—May to September.

*Plant habit*.—Compact mounding habit.

*Plant height*.—20 cm to 24 cm.

*Plant width*.—17 cm to 19 cm.

*Plant hardiness*.—Hardy to minus 15° Centigrade.

*Type*.—Perennial.

*Root system*.—Fibrous.

*Propagation*.—Propagation is accomplished using shoot cuttings.

*Cultural requirements*.—Plant in full sun, well-drained and moderately fertile soil and keep well fertilized and watered.

*Diseases and pests*.—Susceptible to known *Dianthus* pests and disease but no other susceptibilities to pests or disease are known.

*Time required to produce a rooted cutting*.—5 weeks are needed to produce a rooted cutting.

*Temperature recommended for cuttings to produce roots*.—The air temperature needed is a minimum of 15° Centigrade air temperature and base heat of 21° Centigrade.

*Crop time*.—3 to 4 months is needed to produce a finished 1.5-liter container size from a well-rooted cutting.

Stem:

*Shape*.—Cylindrical, solid.

*Dimensions*.—18 cm to 22 cm in length, 0.2 cm diameter.

*Internodes* (*fully grown non-flowering shoot*).—Between 8 and 10 internodes per stem, internode length ranges from 1.5-2.0 cm.

*Surface*.—Glabrous and glaucous.

*Color*.—122C.

*Branching*.—Numerous shoots from the axils of the lower leaves.

Leaf:

*Type*.—Evergreen.

*Dimensions*.—35 mm in length, 5 mm in width.

*Color* (*adaxial and abaxial surfaces*).—Ranges between 189A to 189B.

*Shape*.—Linear.

*Division*.—Simple.

*Apex*.—Acute.

*Base*.—Decurrent.

*Venation*.—Not prominent.

*Margins*.—Entire.

*Attachment*.—Sheathing.

*Arrangement*.—Opposite and spiraling up stem.

*Surfaces* (*adaxial and abaxial*).—Glaucous.

*Stipules*.—Absent.

Flowers:

*Inflorescence*.—Cymose.

*Type*.—Salviform and symmetrical.

*Number*.—2-3 per stem.

*Position*.—Held moderately above foliage.

*Dimensions* (*including calyx*).—28 mm in length and 40 mm in diameter.

*Shape*.—Circular.

*Profile*.—Flat to flat-concave.

*Lastingness*.—10 days at 20° Celsius on the plant; 8 to 10 days off the plant.

*Fragrance*.—Moderate to strong spicy, clove-like.

*Flowering period*.—May to October in Devon, UK.

Peduncle:

*Shape*.—Cylindrical.

*Dimensions*.—10 to 12 cm in length, 2 mm in diameter.

*Surface*.—Glabrous, waxy.

*Strength*.—Erect.

*Color*.—133B and 136B are individually present.

Bud:

*Shape*.—Obovate (when cracking color).

*Color.*—139B at top and 138B at the bottom.
*Anthocyanin.*—Absent.
*Dimensions.*—21 mm in length and 7 mm in width (described when just cracking color).

Corolla:
*Profile.*—Mainly flat but upper part of corolla convex, lower part of corolla concave.
*Corolla diameter.*—40 mm.
*Flower type.*—Semi-double.
*Petal arrangement.*—Apopetalous and overlapping.
*Petal number.*—10.
*Petal dimensions.*—40 mm in length, 25 mm in width.
*Petal margin.*—Fimbriate, indentations 5 mm in depth.
*Petal shape.*—Obdeltoid.
*Petal surface.*—Glabrous.
*Petal apex.*—Fan shaped, markedly fimbriate.
*Petal base.*—Strap shaped, tapering towards base.
*Petal surface texture.*—Glabrous, soft.
*Petal apex.*—Fan shaped, markedly fimbriate.
*Petal base.*—Strap shaped, tapering towards base.
*Color pattern.*—Blade is white with a burgundy band.
*Petal color* (*adaxial surface*).—Ground color of blade: White, whiter than N155A. Color of band around blade: Ranges from 59A to N77A, about 5 mm wide. Color of middle of strap: 145C. Color of base of strap: 145D.
*Petal color* (*abaxial surface*).—Ground color of blade: White, whiter than N155A. Color of middle of strap: 145C. Color of base of strap: 145D.

Calyx:
*Dimensions.*—20 mm in length and 7 mm in width.
*Shape.*—Cylindrical.
*Sepals.*—Fused to 5 mm below the apex.
*Sepal shape.*—Cylindrical, flat profile, parallel sides.
*Number of sepals.*—5.
*Sepal dimensions.*—18 mm in length and 8 mm in width.
*Apex.*—Divided to a depth of 5 mm, apex subacute.
*Base.*—Fused, ovary superior.
*Color of sepals, outer surface.*—137A fading to 137C at base.
*Color of sepals, inner surface.*—137D.
*Anthocyanin.*—Present sometimes.
*Splitting.*—Not observed.

Epicalyx:
*Position.*—Adpressed to calyx.
*Number of bracts.*—1 pair of 2.
*Bracts shape.*—Acute.
*Bracts dimensions.*—9 mm in length and 5 mm in width.
*Bracts color.*—N138B, N138C and 138D are all present.
*Anthocyanin.*—Present.
*Number of bracteoles.*—1 pair of 2.
*Bracteoles shape.*—Acute.
*Bracteoles dimensions.*—9 mm in length and 9 mm in width.
*Bracteoles color.*—N138B, N138C and 138D are all present.
*Bracteoles anthocyanin.*—Present.

Reproductive organs:
*Stamen number.*—10 to 15.
*Stamen dimensions.*—25 mm length and 0.5 mm diameter.
*Color of filaments.*—White.
*Anther number.*—10 to 15.
*Anther dimensions.*—1 mm length and 0.5 mm in diameter.
*Color of anthers.*—White with slight pink hue.
*Anther attachment.*—Dorsifixed.
*Pollen.*—Present.
*Style number.*—2.
*Style shoulder.*—Absent.
*Color of style.*—White.
*Style dimensions.*—15 mm in length and 0.5 mm in width.
*Stigma number.*—One on each style.
*Stigma color.*—White.
*Ovary position.*—Superior.
*Ovary dimensions.*—7 mm in length and 4 mm in diameter.
*Ovary shape.*—Spindle.
*Ovary surface.*—Smooth with very slight longitudinal depressions.
*Ovary color.*—Upper (apical) half 145A, lower (basal) half 145C.

Seed: Seed has not been observed.

I claim:

1. A new and distinct variety of *Dianthus* plant named 'WP13 GIL05' as illustrated and described herein.

* * * * *